(12) United States Patent
Kusano et al.

(10) Patent No.: US 7,897,816 B2
(45) Date of Patent: Mar. 1, 2011

(54) TETRAMINE COMPOUND AND ORGANIC EL DEVICE

(75) Inventors: Shigeru Kusano, Tsukuba (JP); Makoto Koike, Koriyama (JP); Atsushi Takesue, Koriyama (JP); Mitsutoshi Anzai, Kawasaki (JP)

(73) Assignee: Hodogaya Chemical Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/688,253

(22) Filed: Jan. 15, 2010

(65) Prior Publication Data
US 2010/0171080 A1 Jul. 8, 2010

Related U.S. Application Data

(62) Division of application No. 10/584,140, filed as application No. PCT/JP2004/019755 on Dec. 24, 2004.

(30) Foreign Application Priority Data

Dec. 26, 2003 (JP) .................................. 2003-434432

(51) Int. Cl.
*C07C 211/54* (2006.01)
(52) U.S. Cl. ......... 564/434; 564/433; 564/307; 564/308; 564/309
(58) Field of Classification Search .................. 564/307, 564/308, 309, 433, 434
See application file for complete search history.

(56) References Cited

U.S. PATENT DOCUMENTS

| 7,402,701 B2 * | 7/2008 | Kato et al. ..................... 564/434 |
| 2005/0064237 A1 | 3/2005 | Kato et al. |

FOREIGN PATENT DOCUMENTS

| EP | 0 650 955 A1 | 5/1995 |
| JP | 2000 247932 | 9/2000 |
| JP | 2002 167365 | 6/2002 |
| JP | 2002 179630 | 6/2002 |
| JP | 2005-108804 | 4/2005 |

OTHER PUBLICATIONS

Shizuo Tokito, et al. "Thermal Stability of Electroluminescent Devices Fabricated Using Novel Charge-Transporting Materials", American Chemical Society, XP-008038620, vol. 38, No. 1, 1997, pp. 388-389.

Hiromitsu Tomyama, et al. "Electrophotographic Photoconductor Containing Tetramine or Hexamine", STN Database accession No. 126: 111013, XP-002412562, JP 08-292586, Nov. 5, 1996, 3 pages.

Office Action mailed Aug. 31, 2010, in Japanese Patent Application No. 2005-516726 filed on Jun. 26, 2006.

* cited by examiner

*Primary Examiner* — David Wu
*Assistant Examiner* — Vu A Nguyen
(74) *Attorney, Agent, or Firm* — Oblon, Spivak, McClelland, Maier & Neustadt, L.L.P.

(57) ABSTRACT

The present invention provides a tetramine compound represented by the following general formula (1):

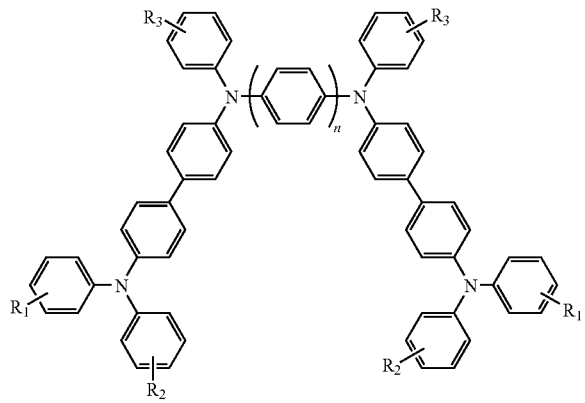

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

2 Claims, 7 Drawing Sheets

TETRAMINE COMPOUND AND ORGANIC EL DEVICE

CROSS REFERENCE TO RELATED APPLICATION

This application is a divisional application of U.S. application Ser. No. 10/584,140, filed on Jun. 26, 2006, which is a 371 of PCT/JP04/19755, filed on Dec. 24, 2004, and claims priority to the following application: Japanese Patent Application No. 2003-434432, filed on Dec. 26, 2003.

TECHNICAL FIELD

The present invention relates to an organic EL element which is a light emitting element having a hole transport layer, a light emitting layer and an electron transport layer and widely utilized as various displays, and which provides high luminance at low applied voltage and is also excellent in stability.

BACKGROUND ART

An organic EL element is a self-luminous element, so that a brighter, clearer display is possible compared to a liquid crystal element. Further, it has useful characteristics such as a wide view angle and high-speed responsibility. Accordingly, studies thereon have been made by many researchers from long ago.

Initially, an organic electroluminescence element using an organic material had been far from a practical level. However, characteristics thereof have been dramatically improved by a laminated structure element developed by C. W. Tang et al of Eastman Kodak Co. in 1987, in which various roles are divided to respective materials. They laminated a fluorescent material which is stable in the structure of its vapor-deposited film and can transport electrons, with organic matter which can transport holes, and injected both carriers into the fluorescent material, thereby succeeding in emitting light. This improved the luminous efficiency of the organic electroluminescence element, resulting in obtaining a high luminance of 1000 $cd/m^2$ or more at a voltage of 10 V or less (for example, see patent document 1 and patent document 2). Thereafter, studies for improving the characteristics were made by many researchers, and at present, the luminous characteristic of a higher luminance of 10000 $cd/m^2$ or more have been obtained concerning light emission for a short period of time.

Patent Document 1: JP-A-8-48656
Patent Document 2: Japanese Patent No. 3194657

At present, the organic EL elements have been put to practical use, and utilized as displays for cell phones, car audios and the like, and it has been further expected to enlarge the size and to expand the use range. However, there are still many problems required to be solved. One of them is heat resistance at the time when they are driven under high temperature environment. α-NPD which has been widely used as a hole transport material at present has a problem in heat resistance, and the use thereof under high temperature environment such as a large-sized display which generates heat upon use or in-vehicle applications which require high durability has been considered to be impossible (for example, see non-patent document 1). Accordingly, concerning a presently employed general element constitution, it has been said that the heat stability of the element is determined by the heat stability of the hole transport material. This is because the hole transport material mainly composed of an organic amine-based material is inevitably disadvantageous in terms of heat stability, when attention is paid to the materials of the respective layers used in organic EL elements. Accordingly, improvements of the heat stability of the hole transport material is considered to lead to improvements of the heat stability of the element. The general element constitution referred to herein indicates one as shown in FIG. 1.

Non-Patent Document 1: M&BE, vol. 11, No. 1 (2000)

DISCLOSURE OF THE INVENTION

The present inventors paid attention to the heat stability of the hole transport material, grasped the glass transition point of a compound deeply concerned with the heat stability of a vapor-deposited film as an important factor, and made studies on materials. The glass transition point is an upper limit temperature at which a substance can exist in an amorphous state, and an important physical property value that determines the film stability of the vapor-deposited film. Theoretically, it can be said that the higher the glass transition point, the higher the heat stability of the element. Further, giving attention also to a molecular structure, it was tried to connect diamine compounds through a plurality of phenyl groups, thereby giving a feature to the molecular structure to improve the stability in an amorphous state.

An object of the invention is to provide an organic EL element having a hole transport layer excellent in luminous stability when driven at a high temperature.

Another object of the invention is to provide an excellent compound as a material used for the hole transport material.

Requirements which the hole transport material should have include (1) having excellent hole transport ability, (2) being thermally stable and stable in the amorphous state, (3) being capable of forming a thin film, (4) being electrically and chemically stable, and (5) not being decomposed at the time of vapor deposition.

In order to achieve the above-mentioned objects, the present inventors variously manufactured EL elements by way of trial, and extensively evaluated newly synthesized hole transport materials, thereby leading to the completion of the invention.

That is, the invention relates to a tetramine compound represented by the following general formula (1):

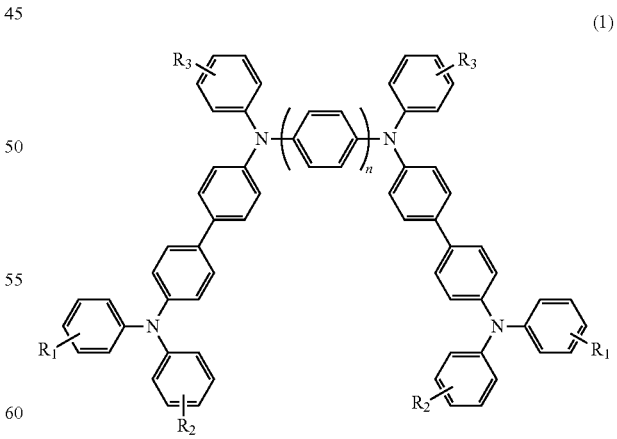

(1)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

Further, the invention relates to an organic EL element material represented by the following general formula (1):

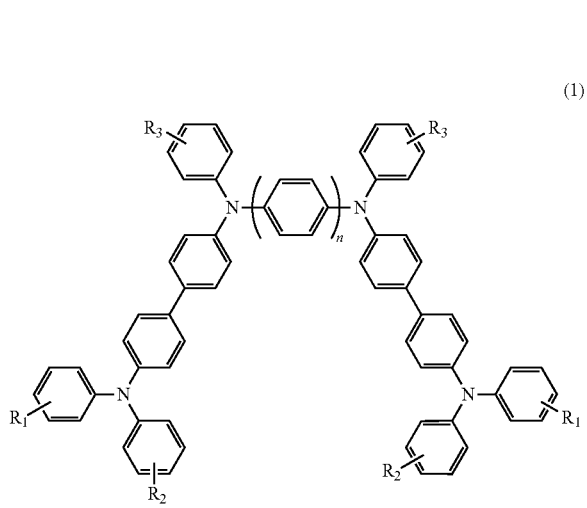
(1)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

Furthermore, the invention relates to an organic EL element containing a tetramine compound represented by the following general formula (1):

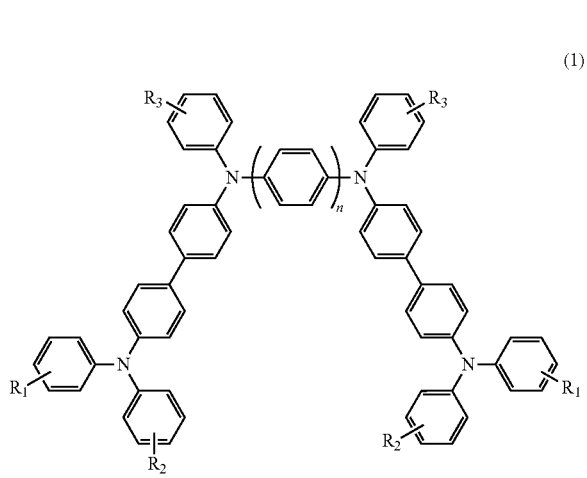
(1)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

Moreover, the invention is a method for producing a tetramine compound represented by general formula (1) shown below, which comprises the step of conducting condensation reaction of a triphenyldiaminobiphenyl compound represented by the below-shown general formula (A) and a dihalogen compound represented by the below-shown general formula (B):

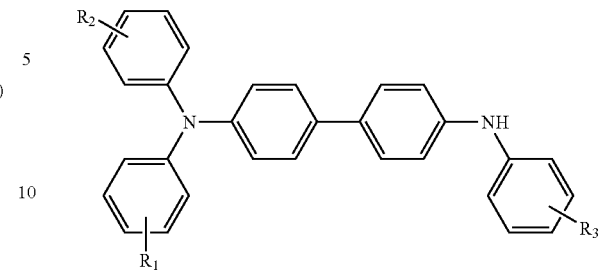
(A)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms;

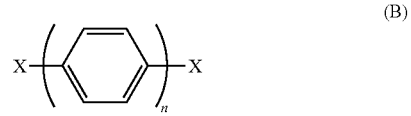
(B)

wherein X represents a halogen atom, and n represents 3 or 4;

(1)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

As another method, the invention also provides a method for producing a tetramine compound represented by general formula (2) shown below, which comprises conducting condensation reaction of a diamino compound represented by the below-shown general formula (C) and a halogen compound represented by the below-shown general formula (D), hydrolyzing a condensation product, and then, further conducting condensation reaction with a halogen compound represented by the below-shown general formula (E):

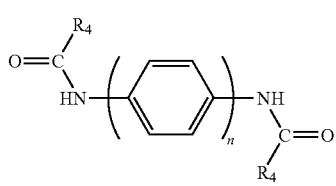

(C)

wherein R4 represents a substituted or unsubstituted alkyl group or a substituted or unsubstituted aryl group, and n represents 3 or 4;

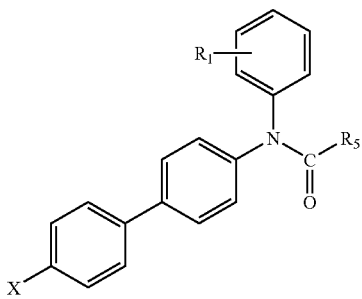

(D)

wherein R1 represents a hydrogen atom, a tertiary alkyl group having 4 to 8 carbon atoms, an unsubstituted aryl group or an aryl group substituted with a tertiary alkyl group having 4 to 8 carbon atoms, R5 represents a substituted or unsubstituted alkyl group or a substituted or unsubstituted aryl group, and X represents a halogen atom;

(E)

wherein R2 represents a hydrogen atom, a tertiary alkyl group having 4 to 8 carbon atoms, an unsubstituted aryl group or an aryl group substituted with a tertiary alkyl group having 4 to 8 carbon atoms, and X represents a halogen atom;

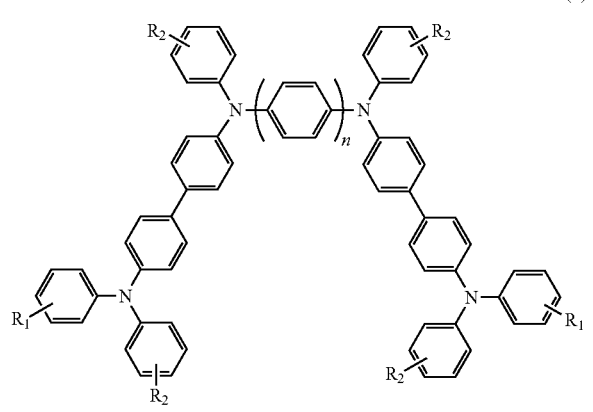

(2)

wherein R1 and R2, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

In the invention, the hole transport material as described above is used. As a result, it not only has excellent hole transport ability, but also forms a good thin film, and further, it is thermally stable. Compared to the case where a conventional hole transport material has been used, the life under high temperature environment has been significantly improved. As a result, it has become clear that the organic EL element having excellent luminous stability can be realized.

As described above, the invention is the organic EL element using the tetramine compound connected through a plurality of phenyl groups as the material for the hole transport layer, and by using the material of the invention, luminous stability at the time of high temperature driving which has been the largest problem of the conventional organic EL element can be markedly improved, making it possible to markedly expand the use range of the organic EL element. For example, development to applications under high temperature environment such as interior illumination, organic semiconductor lasers and in-vehicle applications which require high durability has also become possible.

Figure 1:
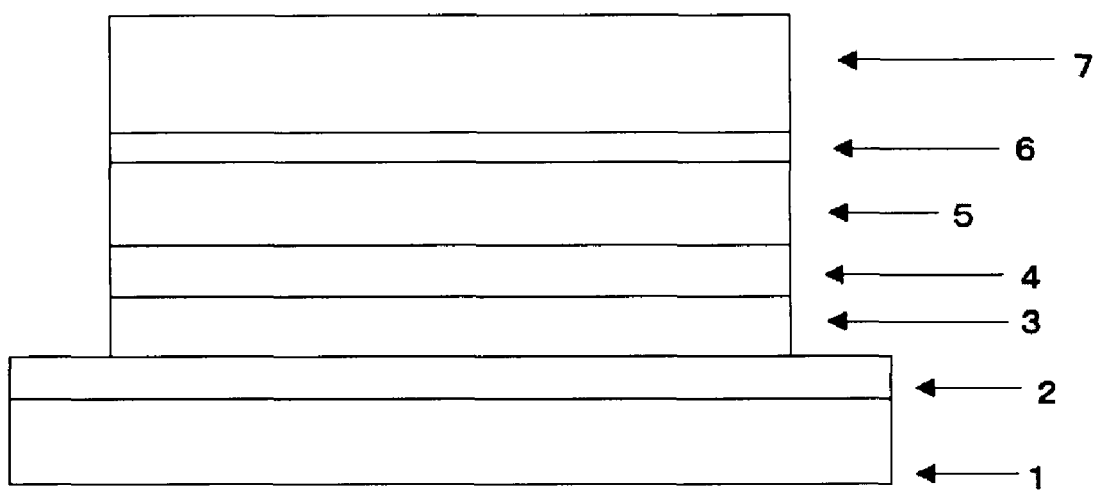
FIG. 1 is a view showing typical EL element constitution.
Figure 2:
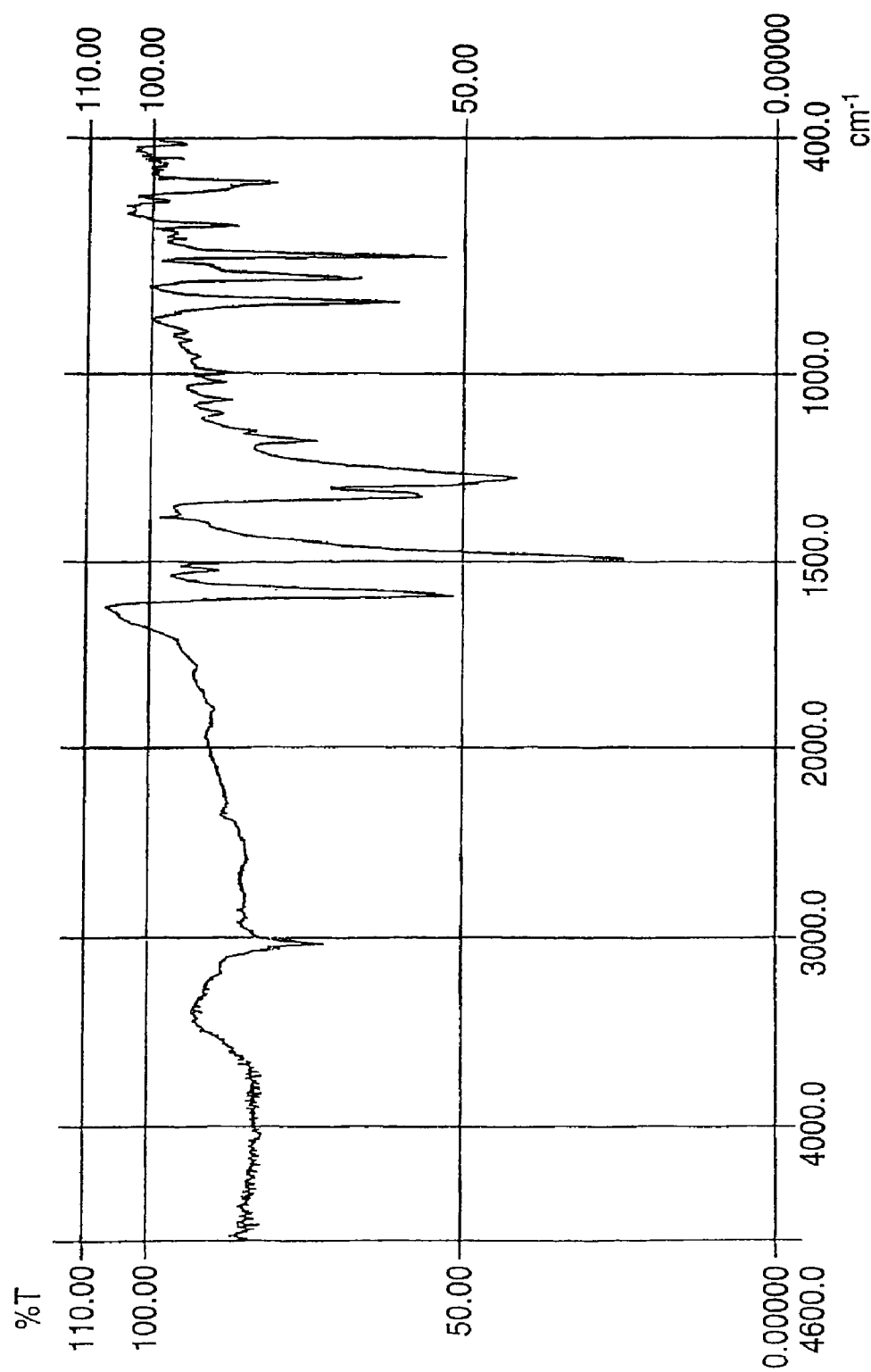
FIG. 2 is an IR chart of HTM-1.
Figure 3:
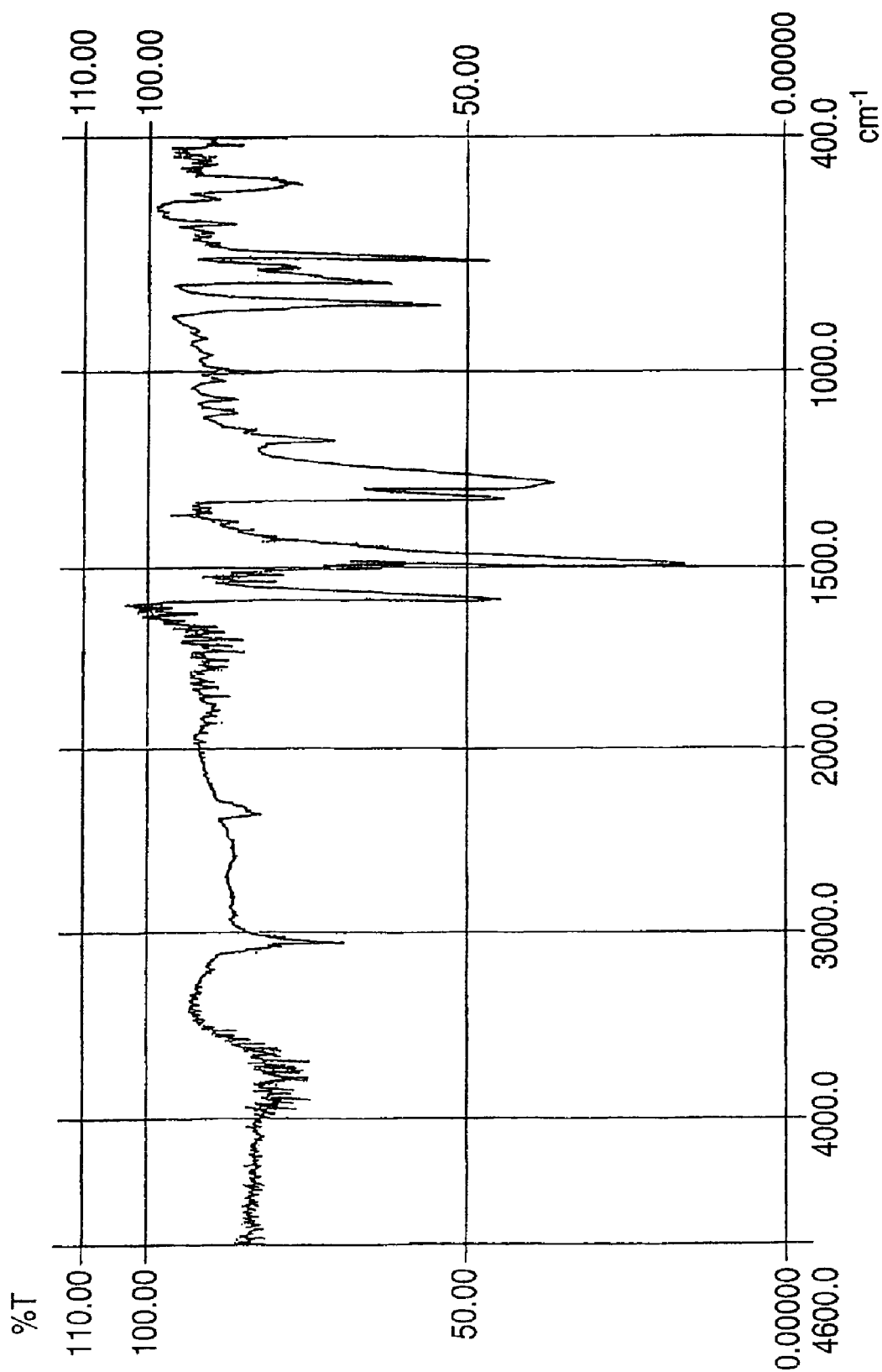
FIG. 3 is an IR chart of HTM-2.
Figure 4:
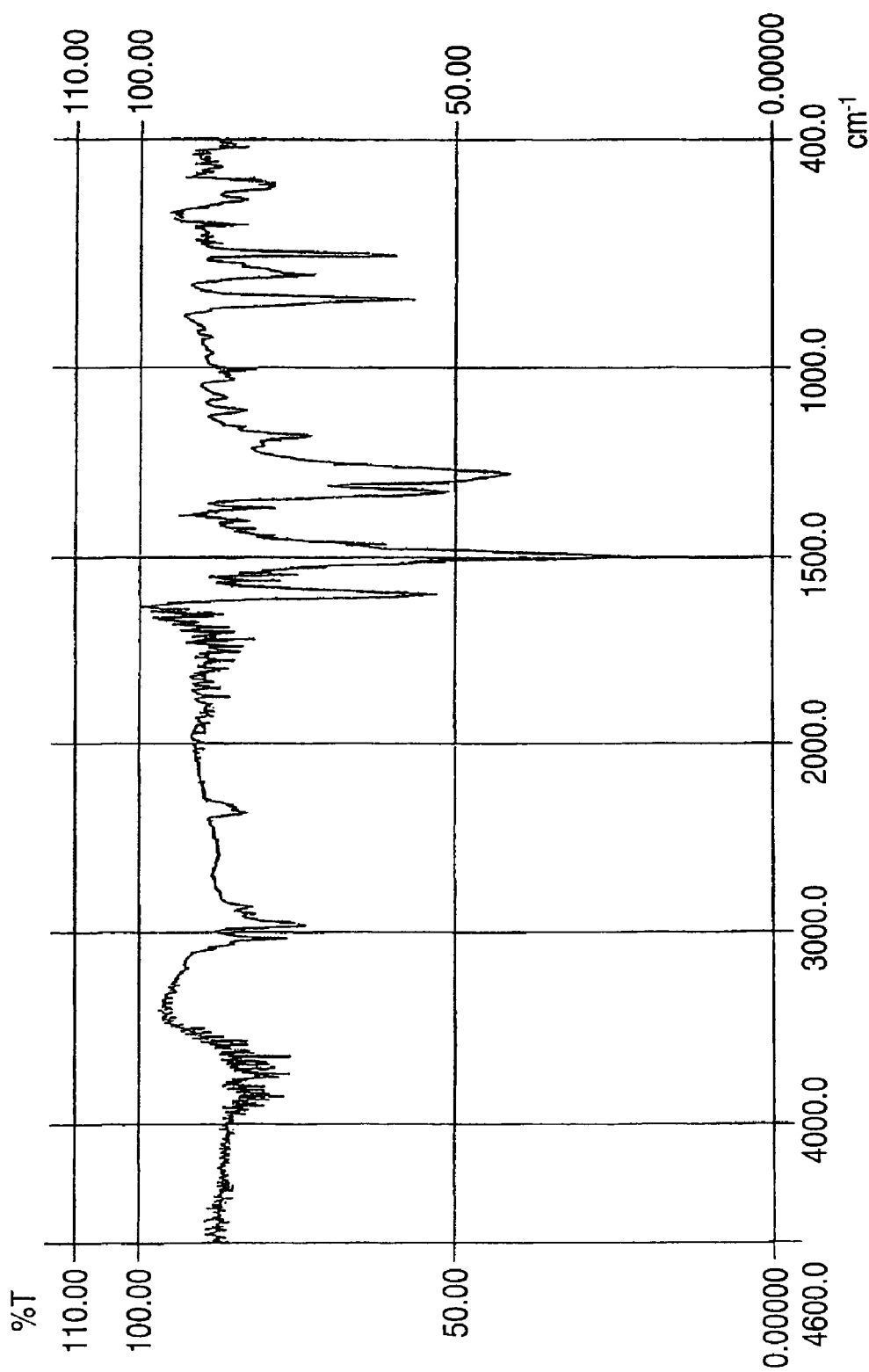
FIG. 4 is an IR chart of HTM-3.
Figure 5:
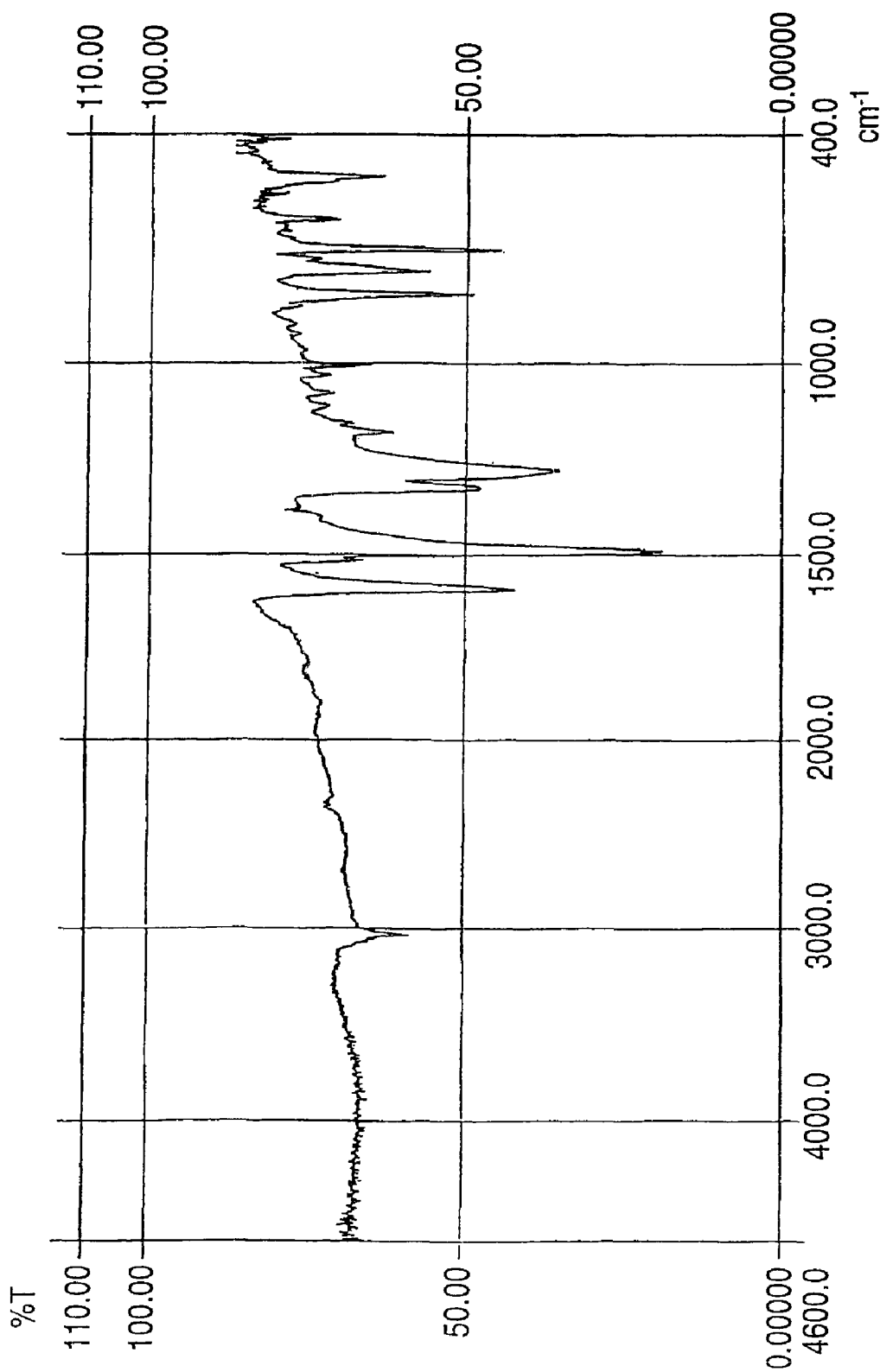
FIG. 5 is an IR chart of HTM-4.
Figure 6:
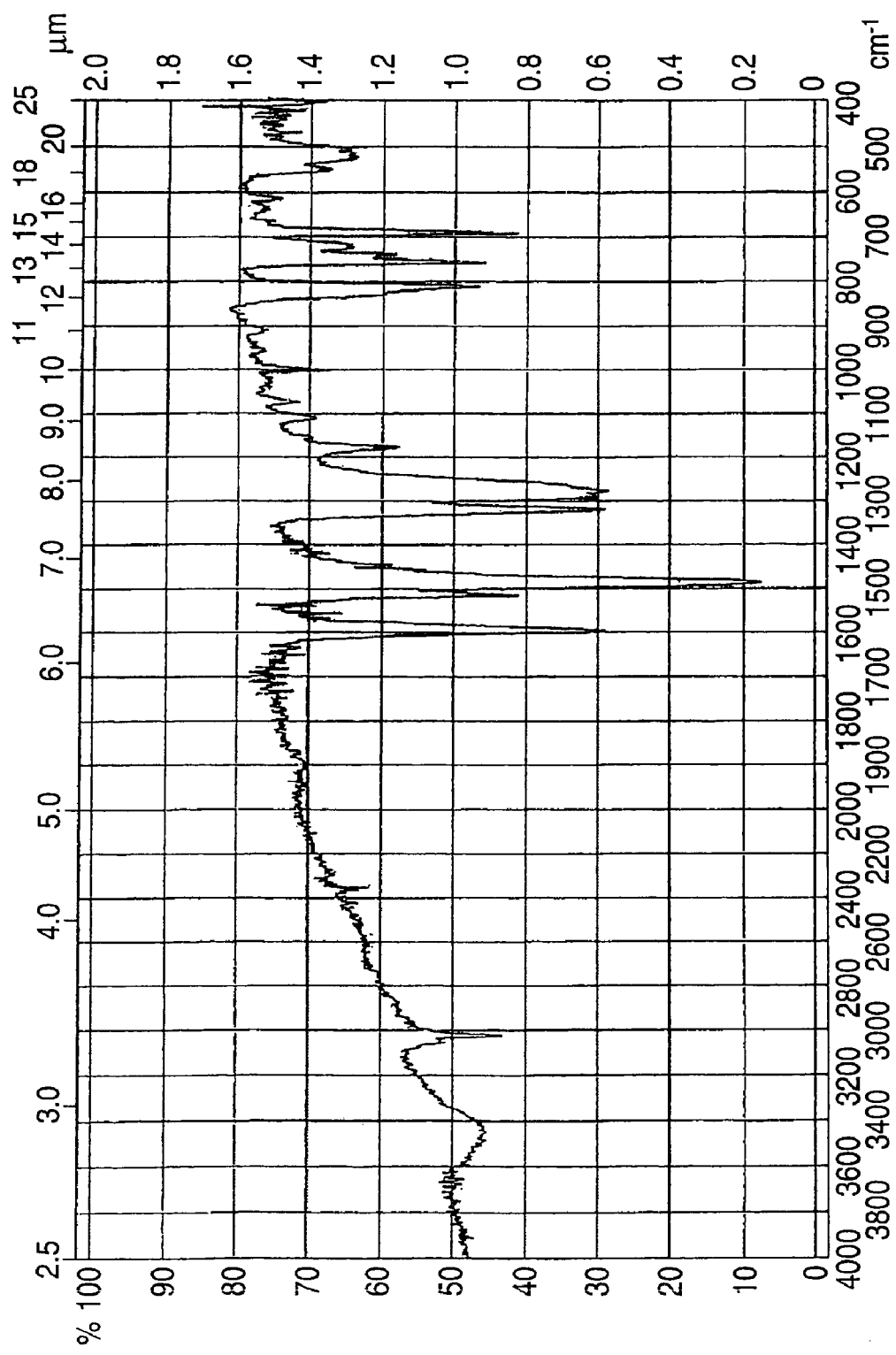
FIG. 6 is an IR chart of HTM-5.
Figure 7:
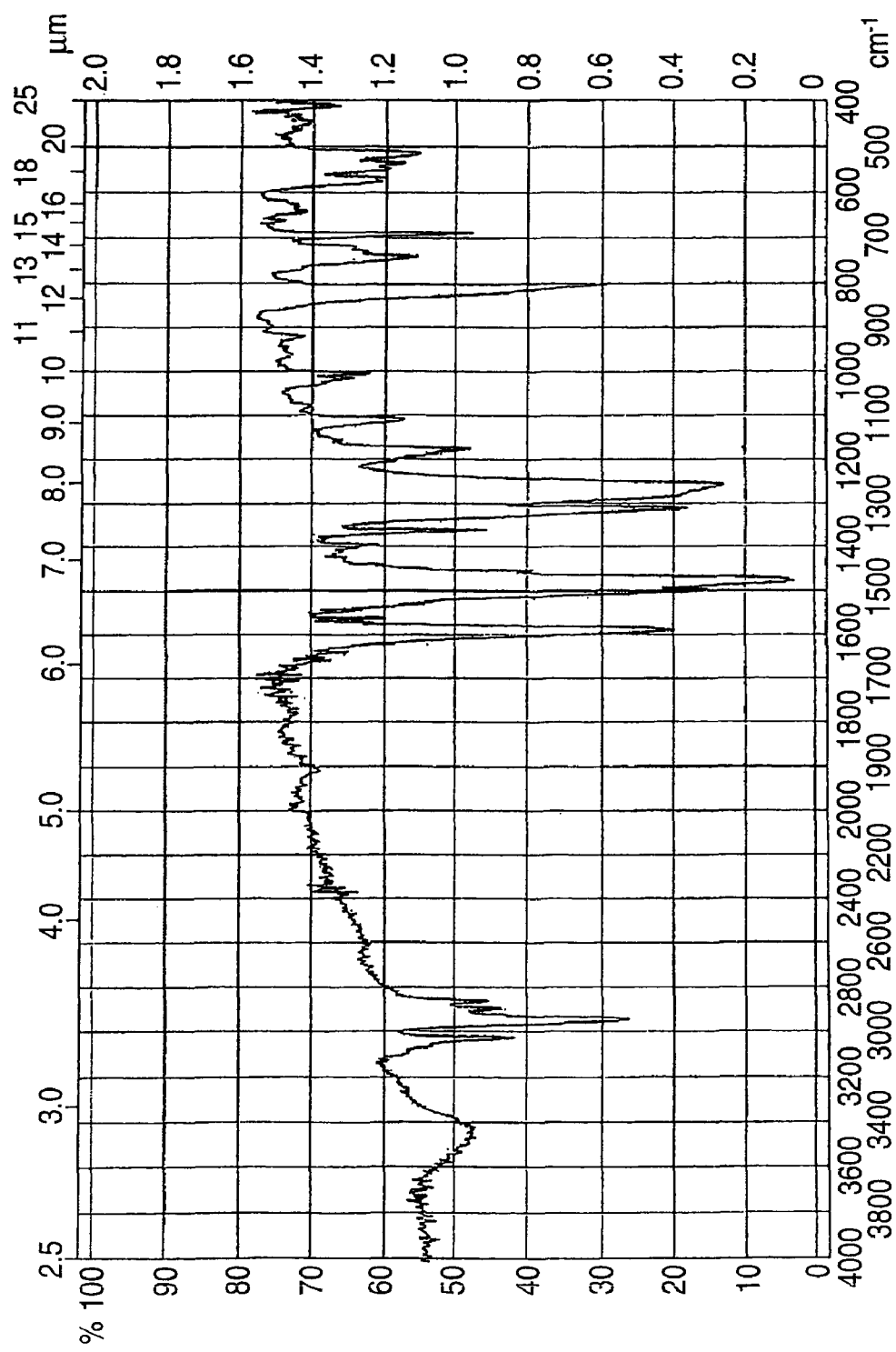
FIG. 7 is an IR chart of HTM-6.

As for reference numerals in the figure, 1 denotes a glass substrate, 2 denotes a transparent anode, 3 denotes a hole injection layer, 4 denotes a hole transport layer, 5 denotes a layer used both as an electron transport layer and as a light emitting layer, 6 denotes a buffer layer, and 7 denotes a cathode.

BEST MODE FOR CARRYING OUT THE INVENTION

The tetramine compound, the hole transport material of the invention, is a novel compound, and this can be synthesized by condensation reaction of a corresponding triphenyldiaminobiphenyl compound and a dihalogen compound, or by hydrolyzing a product obtained by condensation reaction of an N,N'-diacyl form of a corresponding diamine compound and a corresponding N-(4'-halogenated biphenylyl)-N-acylaniline compound, and then, conducting condensation reaction with a corresponding halogenated aryl compound. Such condensation reaction is a production method known as the Ullman reaction.

Identification of these compounds was performed by NMR analysis, elemental analysis and IR analysis. Purification was performed by purification according to column chromatography, adsorption purification according to an adsorbent, or recrystallization or crystallization according to a solvent to a purity of 99.8% or more. Confirmation of the purity was performed by high speed liquid chromatography or a TLC scanner. As physical property values, there were performed DSC measurement (Tg), TG-DTA measurement (decomposition point) and melting point measurement. The melting point and decomposition point act as an index of the heat stability of the hole transport layer, and the glass transition point (Tg) acts as an index of the stability of the glass state.

For the glass transition point (Tg), 5 mg of a sample powder was weighed into an aluminum press cell, set to a DSC apparatus manufactured by SHI while allowing nitrogen gas to flow at 150 ml/min, elevated in temperature up to 400° C. at a rate of 10° C. per minute to melt the sample, then, cooled to −50° C. at a rate of −40° C. per minute, and elevated in temperature again up to 350° C. at a rate of 10° C. per minute. The glass transition point (Tg) was determined from an endothermic change at that time. For the decomposition point, 5 mg of a sample powder was weighed into a platinum cell, set to a TG-DTA apparatus manufactured by SHI while allowing nitrogen gas to flow at 150 ml/min, and elevated in temperature up to 800° C. at a rate of 10° C. per minute. From the resulting chart, a temperature at which a rapid decrease in amount started was taken as the decomposition temperature. For the melting point, a tube bottom of a melting point measuring tube ME-18552 manufactured by Mettler was filled with a sample powder to a length of 10 mm, and elevated in temperature at 1° C. per minute using a melting point measuring device FP-62 manufactured by Mettler. The resulting value was taken as the melting point.

The present inventors synthesized materials, variously changing substituent groups of compounds. As a result, the magnitudes of the melting point, decomposition point and glass transition point vary depending on the substituent group, and in the case of some substituent groups, materials which are high in melting point, decomposition point and glass transition point (Tg) could be obtained. Specific compound examples are shown in Tables 1-1 and 1-2. Further, some typical synthesis examples are shown as examples, but the invention should not be construed as being limited to these compounds.

TABLE 1-1

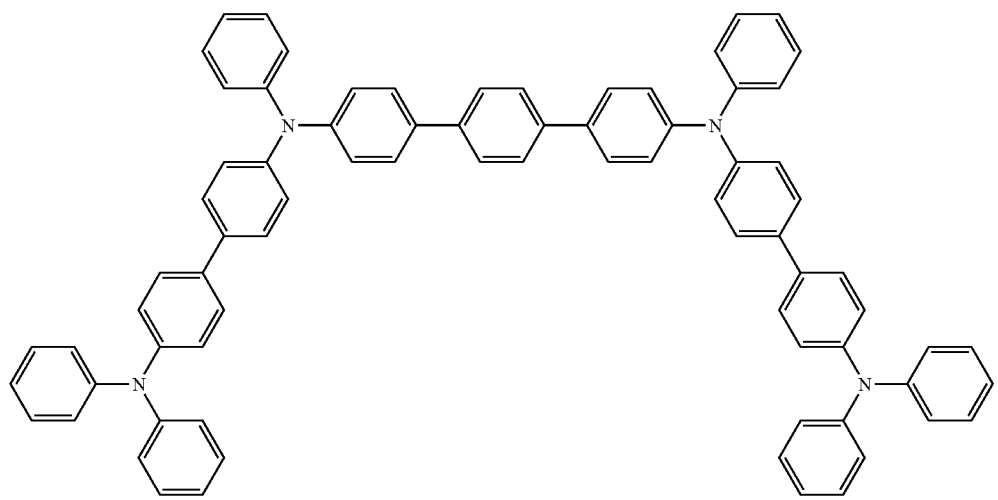

HTM-1

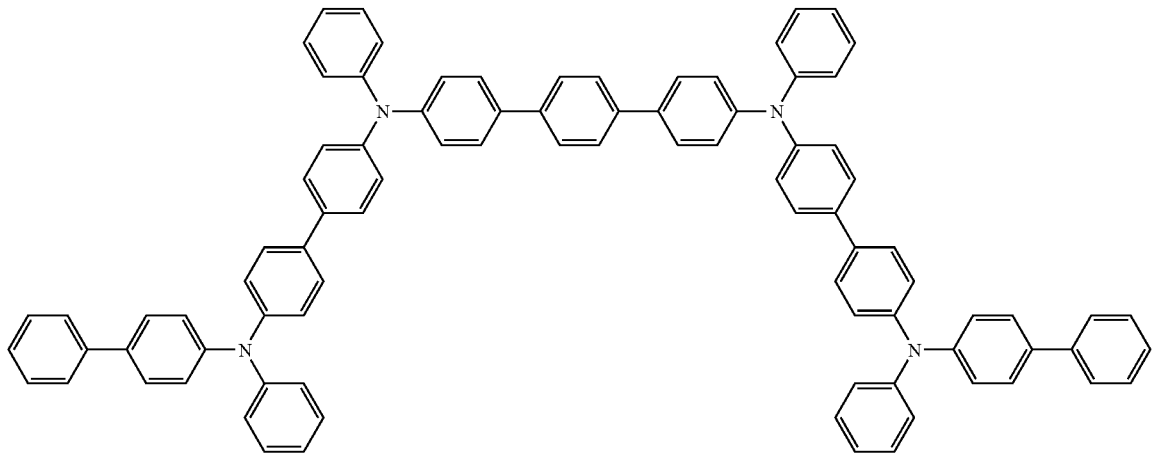

HTM-2

TABLE 1-1-continued
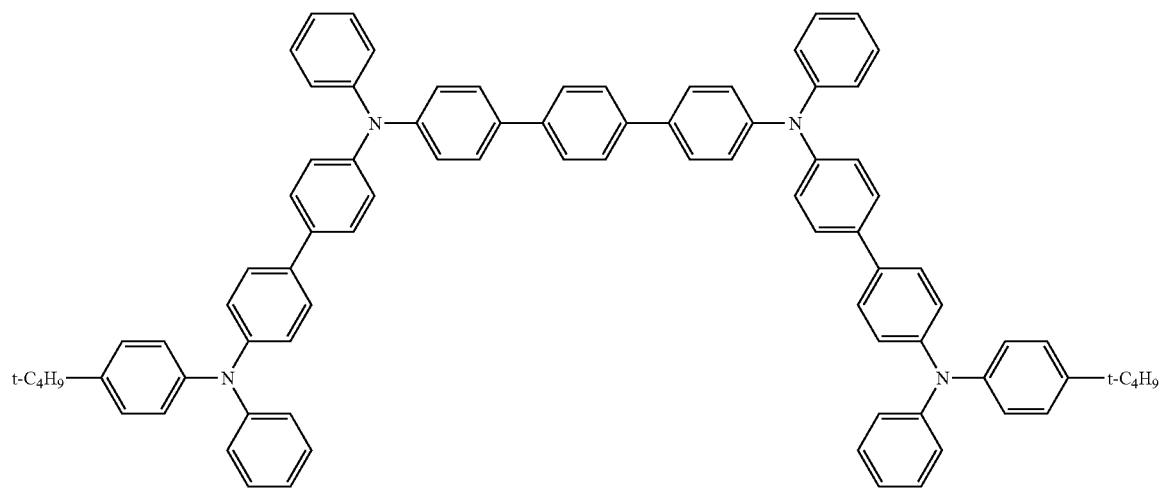
HTM-3
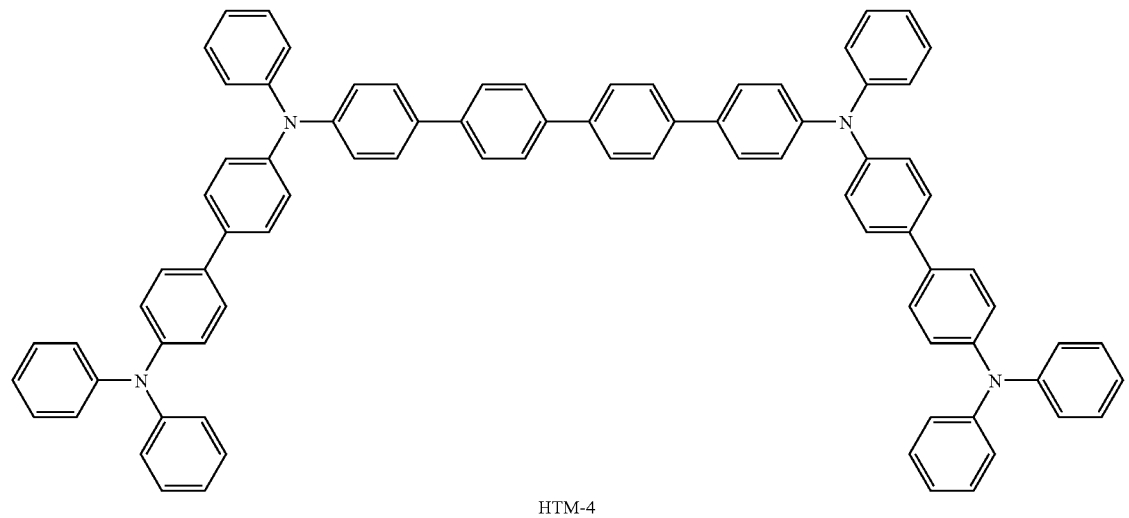
HTM-4
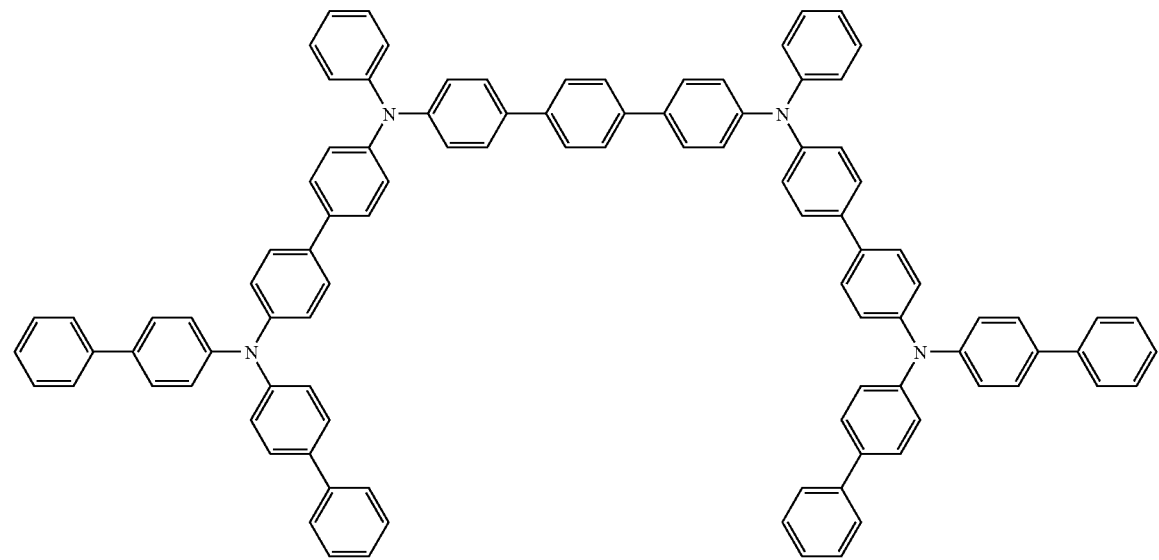
HTM-5

TABLE 1-1-continued
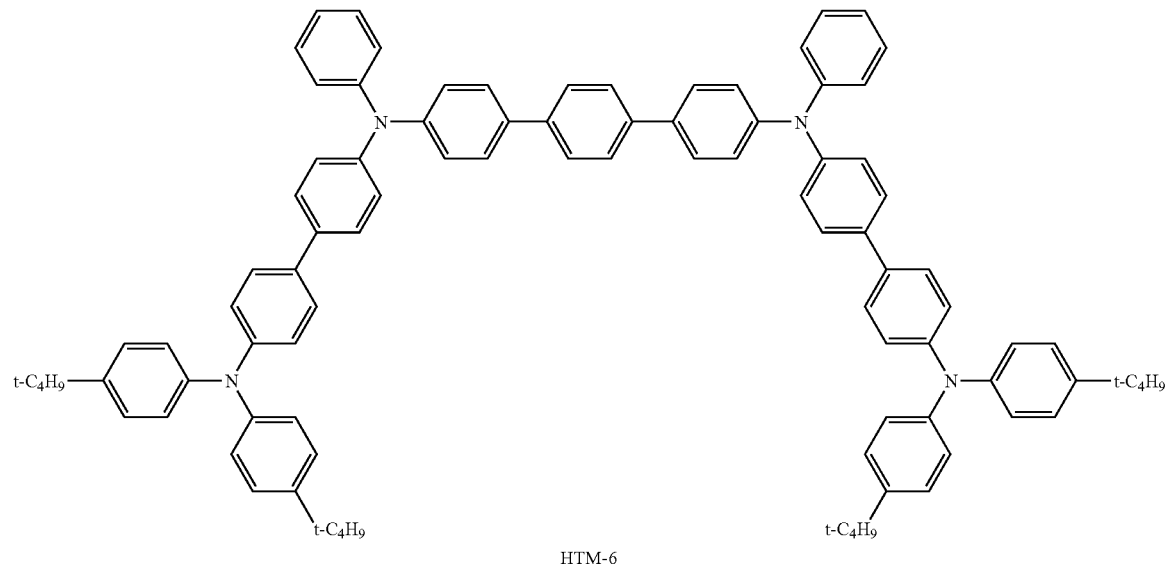
HTM-6
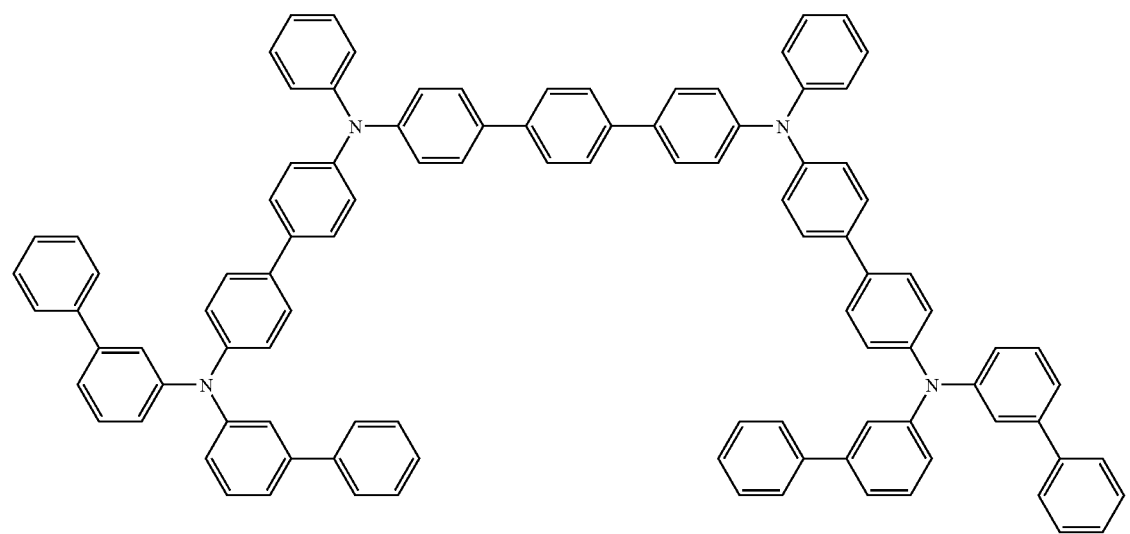
HTM-7

TABLE 1-1-continued
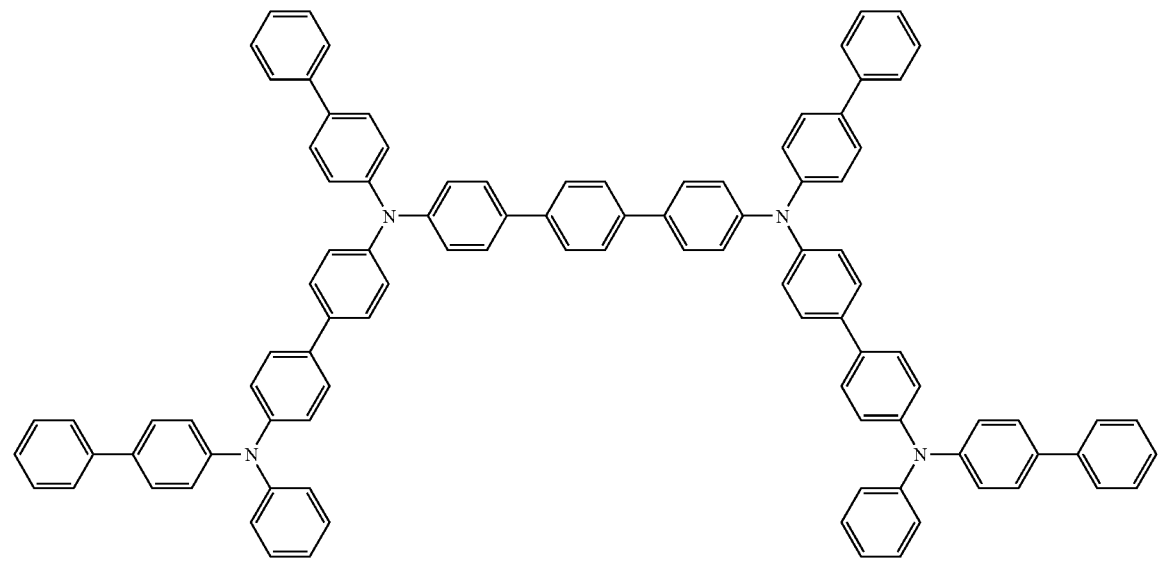
HTM-8
TABLE 1-2
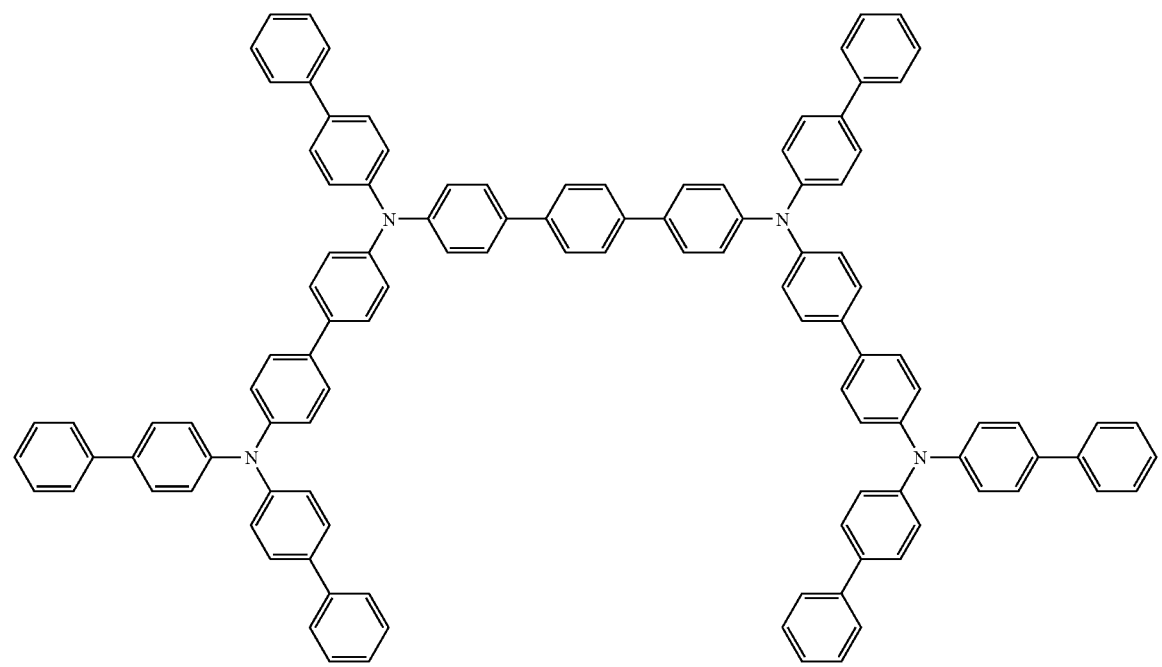
HTM-9

TABLE 1-2-continued
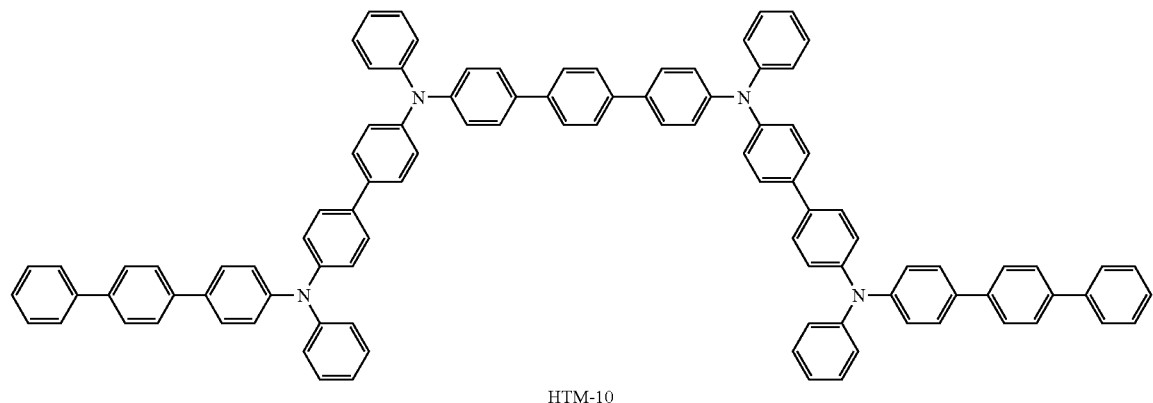
HTM-10
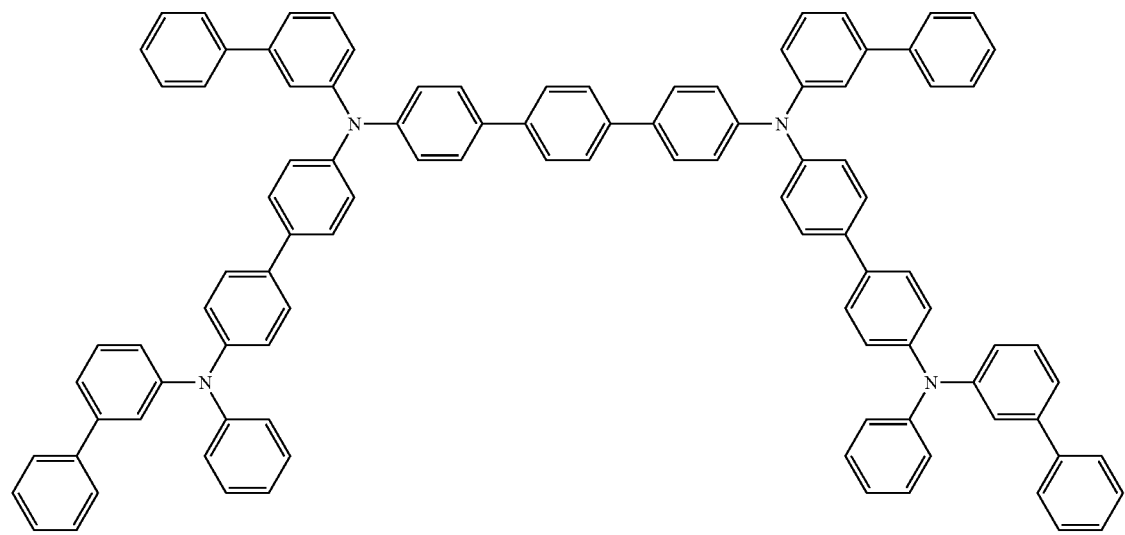
HTM-11
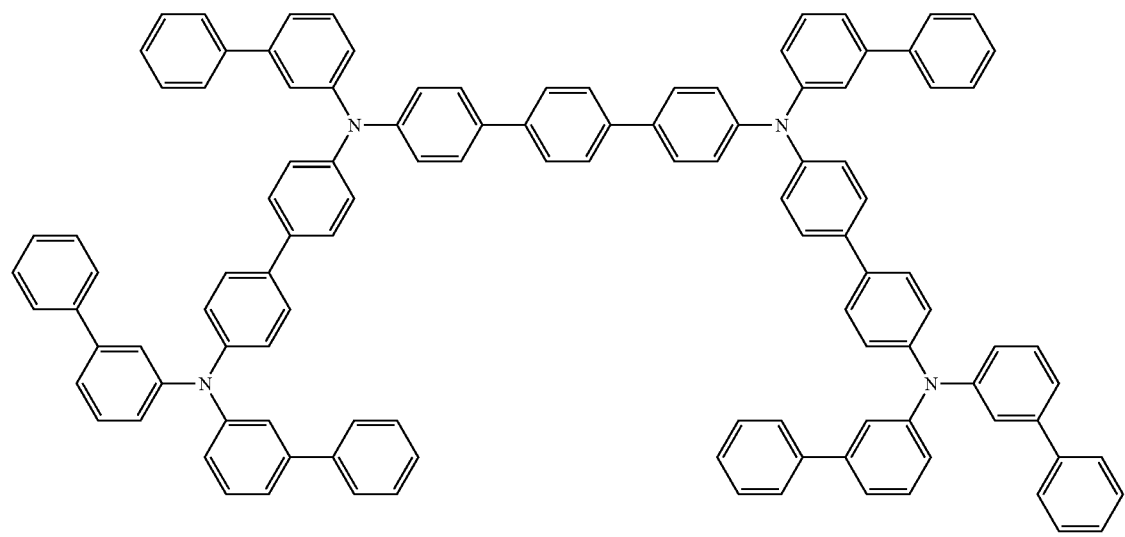
HTM-12

TABLE 1-2-continued
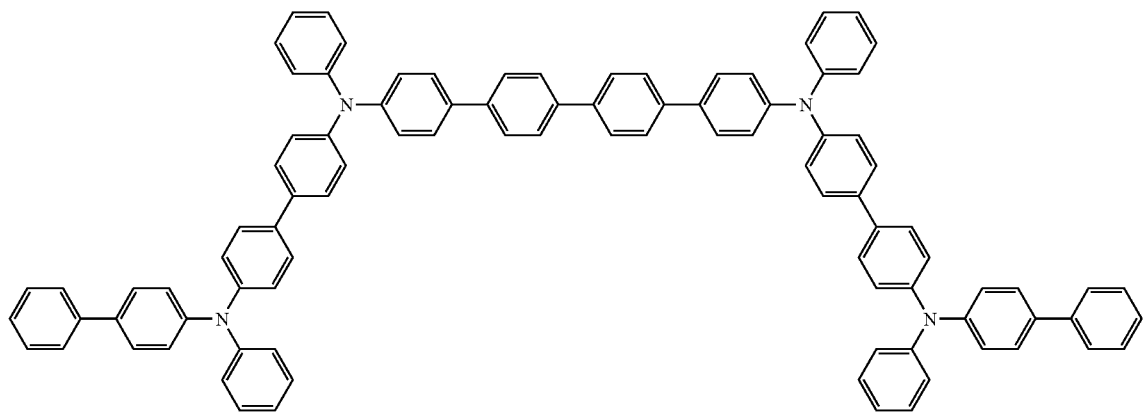
HTM-13
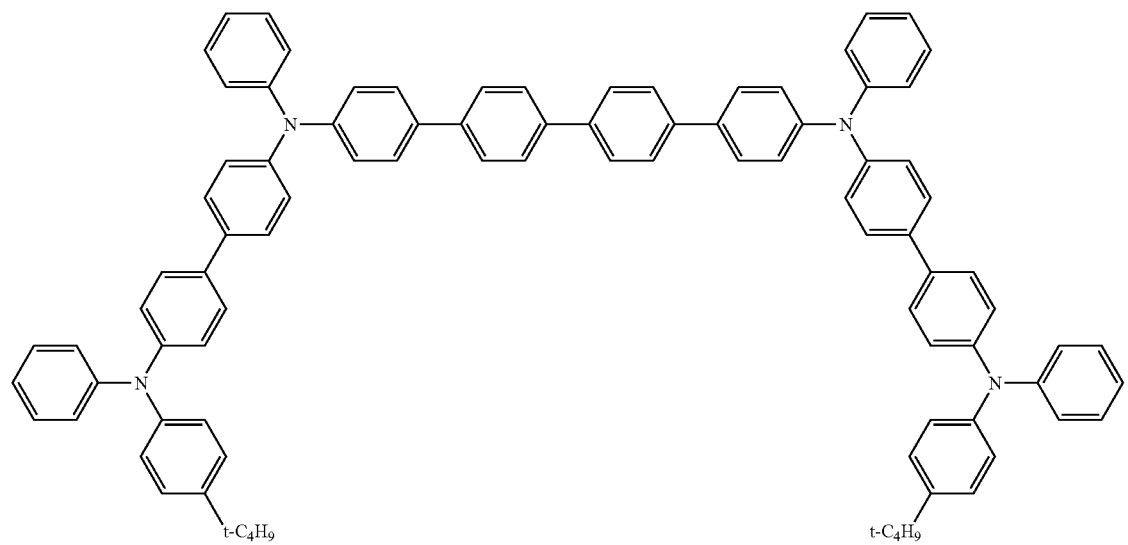
HTM-14
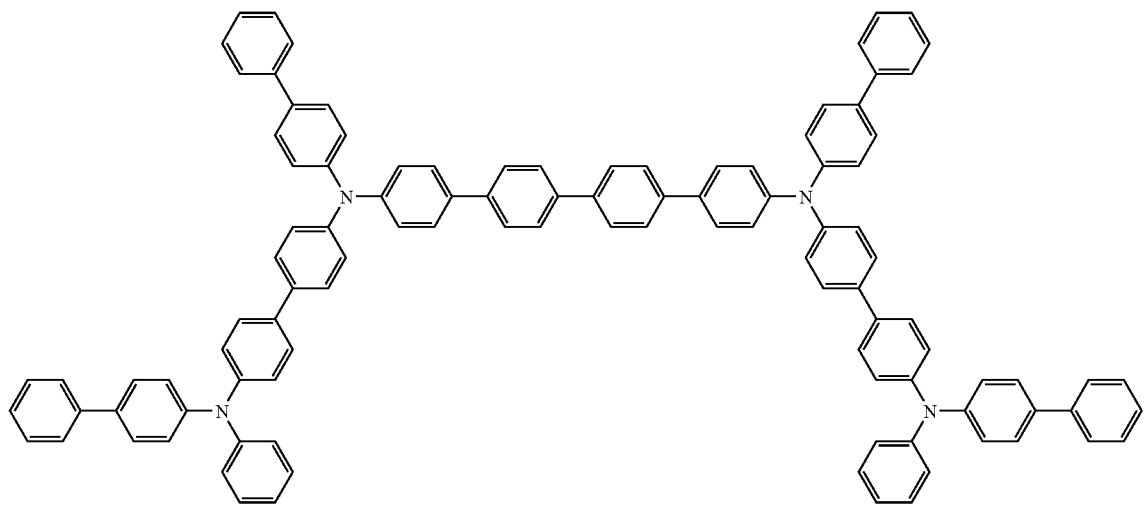
HTM-15

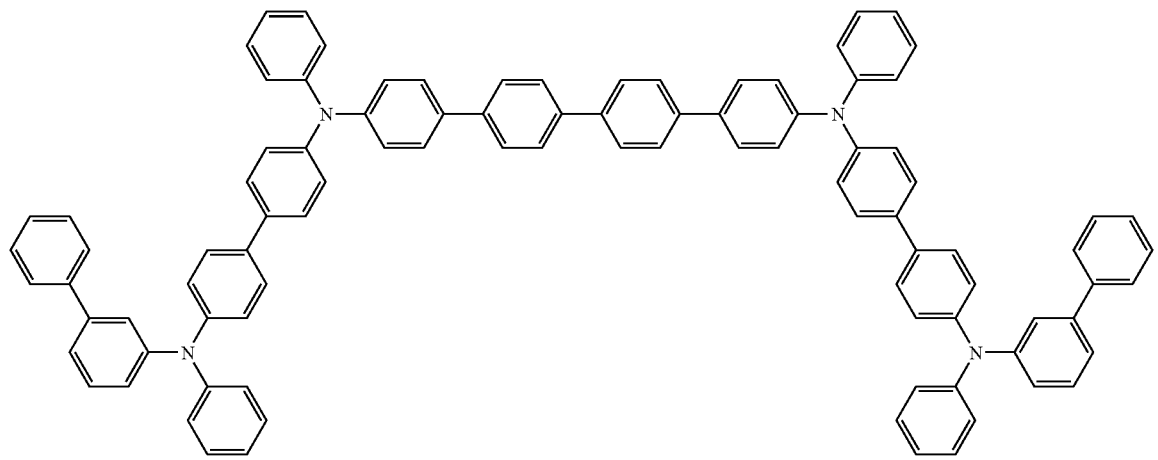

HTM-16

The tetramine compound represented by general formula (1), which was connected through three or four phenyl groups, had a high glass transition point (Tg), and gave a good improving effect on the element life at the time of high temperature driving. Further, in a material into which an unsubstituted aryl group was introduced, a further effective effect was confirmed.

The organic EL element structures of the invention include one comprising an anode, a hole transport layer, a light emitting layer, an electron transport layer and a cathode laminated sequentially on a substrate, or one comprising an anode, a hole transport layer, an electron transport layer and a cathode laminated sequentially on a substrate, wherein either the hole transport layer or the electron transport layer has a light emitting function (serving as a light emitting layer). Further, they include one comprising an ITO electrode, a hole injection layer, a hole transport layer, a light emitting layer, an electron transport layer, a cathode buffer layer and an aluminum electrode.

Further, as the hole transport material according to the invention, only one kind of the tetramine compound represented by general formula (1) can be used. Alternatively, two or more kinds can be used in a mixed state by forming a film by co-deposition or the like. Furthermore, the hole transport material of the invention can be used by co-deposition with TPAC (1,1-bis[4-[N,N-di(p-tolyl)amino]]cyclohexane) or TPD (N,N'-diphenyl-N,N'-di(m-tolyl)benzidine) which is a conventional hole transport material. By using two or more kinds by co-deposition, crystallization thereof can be made difficult to occur in some cases. Moreover, the hole transport layer of the invention may serve as a light emitting layer. Specifically, by combining the hole transport material and an electron transport material having high hole blocking properties, the hole transport layer can be used as a light emitting layer.

Further, the electron transport layer of the invention may serve as a light emitting layer. For the layer of both the electron transport and the light emission according to the invention, there can be used various rare earth complexes, oxazole derivatives, polyparaphenylenevinylenes and the like as materials for the light emitting layer, as well as alumiquinoline trimers.

Furthermore, the higher performance EL element can be prepared by adding a light emitting material called a dopant, such as quinacridone, coumarin or rubrene, to the light emitting layer.

For the hole injection layer, copper phthalocyanine is used. For the cathode buffer layer, lithium fluoride is used.

EXAMPLES

The present invention will be illustrated in greater detail with reference to the following examples, but the invention should not be construed as being limited to these examples.

Synthesis of Hole Transport Materials

Example 1

Synthesis of HTM-1

There were mixed 20.3 g (0.15 mole) of acetanilide, 73.1 g (0.18 mole) of 4,4'-diiodobiphenyl, 22.1 g (0.16 mole) of anhydrous potassium carbonate, 2.16 g (0.034 mole) of copper powder and 35 ml of n-dodecane, followed by reaction at 190 to 205° C. for 10 hours. The reaction product was extracted with 200 ml of toluene, and the insoluble matter was removed by filtration. Then, the filtrate was concentrated to dryness. The resulting solid matter was purified by column chromatography (carrier: silica gel, eluate: toluene/ethyl acetate=6/1) to obtain 40.2 g (yield: 64.8%) of N-(4'-iodobiphenylyl)acetanilide. The melting point was 135.0 to 136.0° C.

There were mixed 13.2 g (0.032 mole) of N-(4'-iodobiphenylyl)acetanilide, 6.60 g (0.039 mole) of N,N-di-phenylamine, 5.53 g (0.040 mole) of anhydrous potassium carbonate, 0.45 g (0.007 mole) of copper powder and 10 ml of n-dodecane, followed by reaction at 200 to 212° C. for 15 hours. The reaction product was extracted with 100 ml of toluene, and the insoluble matter was removed by filtration. Then, the filtrate was concentrated to obtain oily matter. The oily matter was dissolved in 60 ml of isoamyl alcohol, and 1 ml of water and 2.64 g (0.040 mole) of 85% potassium hydroxide were added, followed by hydrolysis at 130° C. After isoamyl alcohol was removed by steam distillation, extraction with 250 ml of toluene was performed, followed by washing with water, drying and concentration. The concentrate was purified by column chromatography (carrier: silica gel, eluate: toluene/n-hexane=1/2) to obtain 10.5 g (yield: 72.2%) of N,N,N'-triphenyl-4,4'-diaminobiphenyl. The melting point was 167.5 to 168.5° C.

There were mixed 8.80 g (0.021 mole) of N,N,N'-triphenyl-4,4'-diaminobiphenyl, 5.00 g (0.01 mole) of 4,4"-diiodo-p-terphenyl, 3.90 g (0.028 mole) of anhydrous potassium carbonate, 0.32 g (0.005 mole) of copper powder, 0.30 g (0.03 mole) of sodium bisulfite and 10 ml of n-dodecane, followed by reaction at 195 to 210° C. for 30 hours. The reaction product was extracted with 450 ml of toluene, and the insoluble matter was removed by filtration. Then, the filtrate was concentrated. To the concentrated solution, 60 ml of methanol was added to perform crystallization, and suction filtration was performed to obtain crude crystals. The crude crystals were dissolved in 50 ml of toluene under reflux, and allowed to cool down to 45° C. Then, 100 ml of ethyl acetate was added dropwise to perform crystallization, thereby obtaining crystals. N,N'-bis(4-diphenylaminobiphenyl-4'-yl)-N,N'-diphenyl-4,4"-diamino-p-terphenyl was obtained in an amount of 5.73 g. The yield was 53.0%, and the HPLC purity was 97.7%. The crystals were purified by column chromatography (carrier: silica gel, eluate: toluene/n-hexane=1/1) to obtain 4.75 g (HPLC purity: 100.0%, column purification yield: 84.8%) of N,N'-bis(4-diphenylaminobiphenyl-4'-yl)-N,N'-diphenyl-4,4"-diamino-p-terphenyl. The melting point was 164.8° C. Identification of the product was performed by NMR analysis, elemental analysis and IR analysis. The elemental analysis values are as follows: carbon; measured value; 88.92% (theoretical value; 89.11%), hydrogen; measured value; 5.78% (theoretical value; 5.56%), nitrogen; measured value; 5.07% (theoretical value; 5.33%). The results of NMR analysis were as follows: 7.629 ppm (4H), 7.545-7.449 (12H), 7.313-6.987 ppm (42H).

Example 2

Synthesis of HTM-2

There were mixed 16.5 g (0.040 mole) of N-(4'-iodobiphenylyl)acetanilide, 11.8 g (0.048 mole) of N-(4-biphenyl)aniline, 8.3 g (0.060 mole) of anhydrous potassium carbonate, 0.1 g (0.002 mole) of copper powder and 10 ml of n-dodecane, followed by reaction at 200 to 212° C. for 15 hours. The reaction product was extracted with 200 ml of toluene, and the insoluble matter was removed by filtration. Then, the filtrate was concentrated to obtain oily matter. The oily matter was dissolved in 60 ml of isoamyl alcohol, and 4 ml of water and 4.00 g (0.060 mole) of 85% potassium hydroxide were added, followed by hydrolysis at 130° C. After isoamyl alcohol was removed by steam distillation, extraction with 250 ml of toluene was performed, followed by washing with water, drying and concentration. The concentrate was purified by column chromatography (carrier: silica gel, eluate: toluene/n-hexane=1/2) to obtain 15.2 g (yield: 77.8%, HPLC purity: 97.0%) of N-(4-biphenylyl)-N,N'-diphenyl-4,4'-diaminobiphenyl. The melting point was 126.6 to 127.4° C.

There were mixed 11.08 g (0.022 mole) of N-(4-biphenylyl)-N,N'-diphenyl-4,4'-diaminobiphenyl, 5.00 g (0.01 mole) of 4,4"-diiodo-p-terphenyl, 4.14 g (0.030 mole) of anhydrous potassium carbonate, 0.32 g (0.005 mole) of copper powder and 10 ml of n-dodecane, followed by reaction at 195 to 210° C. for 30 hours. The reaction product was extracted with 400 ml of toluene, and the insoluble matter was removed by filtration. Then, the filtrate was concentrated. To the concentrated solution, 60 ml of methanol was added to perform crystallization, and suction filtration was performed to obtain crude crystals. The crude crystals were dissolved in 50 ml of toluene under reflux, and allowed to cool down to 45° C. Then, 100 ml of ethyl acetate was added dropwise to perform crystallization, thereby obtaining crystals. N,N'-bis[4-(4-biphenylylphenylamino)biphenyl-4'-yl]-N,N'-diphenyl-4,4"-diamino-p-terphenyl was obtained in an amount of 7.91 g. The yield was 65.7%, and the HPLC purity was 96.6%.

The crystals were purified by column chromatography (carrier: silica gel, eluate: toluene/n-hexane=1/1) to obtain 4.30 g (HPLC purity: 100.0%, column purification yield: 56.3%) of N,N'-bis[4-(4-biphenylylphenylamino)biphenyl-4'-yl]-N,N'-diphenyl-4,4"-diamino-p-terphenyl. The melting point was 189.3° C. Identification of the product was performed by NMR analysis, elemental analysis and IR analysis. The elemental analysis values are as follows: carbon; measured value; 89.98% (theoretical value; 89.82%), hydrogen; measured value; 5.61% (theoretical value; 5.53%), nitrogen; measured value; 4.35% (theoretical value; 4.66%). The results of NMR analysis were as follows: 7.637 ppm (4H), 7.594-7.388 (24H), 7.328-7.160 ppm (34H), 7.073-7.025 ppm (4H).

Example 3

Synthesis of HTM-3

There were mixed 20.70 g (0.050 mole) of N-(4'-iodobiphenylyl)acetanilide, 13.50 g (0.060 mole) of 4-tert-butyldiphenylamine, 10.40 g (0.075 mole) of anhydrous potassium carbonate, 0.20 g (0.003 mole) of copper powder and 10 ml of n-dodecane, followed by reaction at 200 to 212° C. for 15 hours. The reaction product was extracted with 200 ml of toluene, and the insoluble matter was removed by filtration. Then, the filtrate was concentrated to obtain oily matter. The oily matter was dissolved in 80 ml of isoamyl alcohol, and 5 ml of water and 5.00 g (0.075 mole) of 85% potassium hydroxide were added, followed by hydrolysis at 130° C. After isoamyl alcohol was removed by steam distillation, extraction with 250 ml of toluene was performed, and the organic layer was washed with water, dried and concentrated. The concentrate was purified by column chromatography (carrier: silica gel, eluate: toluene/n-hexane=1/2) to obtain 18.8 g (yield: 73.5%, HPLC purity: 98.0%) of N-(4-tert-butylphenyl)-N,N'-diphenyl-4,4'-diaminobiphenyl. The melting point was 125.6 to 126.6° C.

There were mixed 11.50 g (0.022 mole) of N-(4-tert-butylphenyl)-N,N'-diphenyl-4,4'-diaminobiphenyl, 5.00 g (0.01 mole) of 4,4"-diiodo-p-terphenyl, 4.14 g (0.030 mole) of anhydrous potassium carbonate, 0.32 g (0.005 mole) of copper powder and 10 ml of n-dodecane, followed by reaction at 195 to 210° C. for 30 hours. The reaction product was extracted with 400 ml of toluene, and the insoluble matter was removed by filtration. Then, the filtrate was concentrated. After the concentration, 60 ml of methanol was added to perform crystallization, and suction filtration was performed to obtain crude crystals. The crude crystals were dissolved in 50 ml of toluene under reflux, and allowed to cool down to 45° C. Then, 100 ml of ethyl acetate was added dropwise to perform crystallization, thereby obtaining crystals. N,N'-bis[4-(4-tert-butyldiphenylamino)biphenyl-4'-yl]-N,N'-diphenyl-4,4"-diamino-p-terphenyl was obtained in an amount of 6.70 g. The yield was 57.5%, and the HPLC purity was 95.6%.

The crystals were purified by column chromatography (carrier: silica gel, eluate: toluene/n-hexane=1/2) to obtain 4.00 g (HPLC purity: 99.9%, column purification yield: 62.5%) of N,N'-bis[4-(4-tert-butyldiphenylamino)biphenyl-4'-yl]-N,N'-diphenyl-4,4"-diamino-p-terphenyl. The melting point was 209.5° C. Identification of the product was performed by NMR analysis, elemental analysis and IR analysis. The elemental analysis values are as follows: carbon; measured value; 88.96% (theoretical value; 88.77%), hydrogen;

measured value; 6.65% (theoretical value; 6.41%), nitrogen; measured value; 4.57% (theoretical value; 4.82%). The results of NMR analysis were as follows: 7.629 ppm (4H), 7.545-7.425 (12H), 7.283-7.033 ppm (40H), 1.317 ppm (18H).

Example 4

Synthesis of HTM-4

There were mixed 8.10 g (0.019 mole) of N,N,N'-triphenyl-4,4'-diaminobiphenyl, 4.00 g (0.008 mole) of 4,4'''-diiodo-p-quaterphenyl, 3.90 g (0.028 mole) of anhydrous potassium carbonate, 0.32 g (0.005 mole) of copper powder, 0.30 g (0.03 mole) of sodium bisulfite and 10 ml of n-dodecane, followed by reaction at 195 to 210° C. for 30 hours. The reaction product was extracted with 450 ml of toluene, and the insoluble matter was removed by filtration. Then, the filtrate was concentrated. After the concentration, 60 ml of methanol was added to perform crystallization, and suction filtration was performed to obtain crude crystals. The crude crystals were dissolved in 50 ml of toluene under reflux, and allowed to cool down to 45° C. Then, 100 ml of ethyl acetate was added dropwise to perform crystallization, thereby obtaining crystals. N,N'-bis(4-diphenylaminobiphenyl-4-yl)-N,N'-diphenyl-4,4'''-diamino-p-quaterphenyl was obtained in an amount of 5.08 g. The yield was 56.4%, and the HPLC purity was 97.5%.

The crystals were purified by column chromatography (carrier: silica gel, eluate: toluene/n-hexane=2/3) to obtain 3.28 g (HPLC purity: 99.8%, column purification yield: 66.0%) of N,N'-bis(4-diphenylaminobiphenyl-4-yl)-N,N'-diphenyl-4,4'''-diamino-p-quaterphenyl. The melting point was 173.1° C. Identification of the product was performed by NMR analysis, elemental analysis and IR analysis. The elemental analysis values are as follows: carbon; measured value; 89.23% (theoretical value; 89.49%), hydrogen; measured value; 5.70% (theoretical value; 5.54%), nitrogen; measured value; 4.76% (theoretical value; 4.97%). The results of NMR analysis were as follows: 7.719-7.639 ppm (8H), 7.555-7.437 (12H), 7.319-6.989 ppm (42H).

Example 5

Synthesis of HTM-5

There were mixed 20.70 g (0.050 mole) of N-(4'-iodobiphenylyl)acetanilide, 19.95 g (0.060 mole) of N,N-bis(biphenyl-4-yl)amine, 10.40 g (0.075 mole) of anhydrous potassium carbonate, 0.20 g (0.003 mole) of copper powder and 10 ml of n-dodecane, followed by reaction at 200 to 212° C. for 15 hours. The reaction product was extracted with 200 ml of toluene, and the insoluble matter was removed by filtration. Then, the filtrate was concentrated to obtain crude crystals. The crude crystals were dissolved in 80 ml of isoamyl alcohol, and 5 ml of water and 5.00 g (0.075 mole) of 85% potassium hydroxide were added, followed by hydrolysis at 130° C. After isoamyl alcohol was removed by steam distillation, extraction with 250 ml of toluene was performed, and the organic layer was washed with water, dried and concentrated. The concentrate was purified by column chromatography (carrier: silica gel, eluate: toluene/n-hexane=1/2) to obtain 24.2 g (yield: 69.9%, HPLC purity: 98.0%) of N,N-bis(biphenyl-4-yl)-N'-phenyl-4,4'-diaminobiphenyl. The melting point was 145.8 to 146.0° C.

There were mixed 12.68 g (0.022 mole) of N,N-bis(biphenyl-4-yl)-N'-phenyl-4,4'-diaminobiphenyl, 5.00 g (0.01 mole) of 4,4''-diiodo-p-terphenyl, 4.14 g (0.030 mole) of anhydrous potassium carbonate, 0.32 g (0.005 mole) of copper powder and 10 ml of n-dodecane, followed by reaction at 195 to 210° C. for 30 hours. The reaction product was extracted with 800 ml of toluene, and the insoluble matter was removed by filtration. Then, the filtrate was concentrated. After the concentration, 100 ml of methanol was added to perform crystallization, and suction filtration was performed to obtain crude crystals. The crude crystals were dissolved in 300 ml of toluene under reflux, and allowed to cool down to 45° C. Then, 300 ml of ethyl acetate was added dropwise to perform crystallization, thereby obtaining crystals. N,N'-bis[4-{bis(biphenyl-4-yl)amino}biphenyl-4'-yl]-N,N'-diphenyl-4,4''-diamino-p-terphenyl was obtained in an amount of 9.43 g. The yield was 65.9%, and the HPLC purity was 94.7%. The crystals were purified by column chromatography (carrier: silica gel, eluate: toluene/n-hexane=1/2) to obtain 5.47 g (HPLC purity: 100.0%, column purification yield: 61.3%) of N,N'-bis[4-{bis(biphenyl-4-yl)amino}biphenyl-4'-yl]-N,N'-diphenyl-4,4''-diamino-p-terphenyl. The melting point was 204.5° C. Identification of the product was performed by NMR analysis, elemental analysis and IR analysis. The elemental analysis values are as follows: carbon; measured value; 90.22% (theoretical value; 90.37%), hydrogen; measured value; 5.73% (theoretical value; 5.50%), nitrogen; measured value; 4.05% (theoretical value; 4.13%). The results of NMR analysis were as follows: 7.637-7.396 ppm (40H), 7.336-7.172 (32H), 7.081-7.029 ppm (2H).

Example 6

Synthesis of HTM-6

There were mixed 20.70 g (0.050 mole) of N-(4'-iodobiphenylyl)acetanilide, 16.88 g (0.060 mole) of N,N-bis(4-tert-butylphenyl)amine, 10.40 g (0.075 mole) of anhydrous potassium carbonate, 0.20 g (0.003 mole) of copper powder and 10 ml of n-dodecane, followed by reaction at 200 to 212° C. for 15 hours. The reaction product was extracted with 200 ml of toluene, and the insoluble matter was removed by filtration. Then, the filtrate was concentrated to obtain oily matter. The oily matter was dissolved in 80 ml of isoamyl alcohol, and 5 ml of water and 5.00 g (0.075 mole) of 85% potassium hydroxide were added, followed by hydrolysis at 130° C. After isoamyl alcohol was removed by steam distillation, extraction with 250 ml of toluene was performed, and the organic layer was washed with water, dried and concentrated. The concentrate was purified by column chromatography (carrier: silica gel, eluate: toluene/n-hexane=1/2) to obtain 20.21 g (yield: 75.5%, HPLC purity: 98.0%) of N,N-bis(4-tert-butylphenyl)-N'-phenyl-4,4'-diaminobiphenyl. The melting point was 161.1 to 162.0° C.

There were mixed 11.78 g (0.022 mole) of N,N-bis(4-tert-butylphenyl)-N'-phenyl-4,4'-diaminobiphenyl, 5.00 g (0.01 mole) of 4,4''-diiodo-p-terphenyl, 4.14 g (0.030 mole) of anhydrous potassium carbonate, 0.32 g (0.005 mole) of copper powder and 10 ml of n-dodecane, followed by reaction at 195 to 210° C. for 30 hours. The reaction product was extracted with 400 ml of toluene, and the insoluble matter was removed by filtration. Then, the filtrate was concentrated. After the concentration, 60 ml of methanol was added to perform crystallization, and suction filtration was performed to obtain crude crystals. The crude crystals were dissolved in 50 ml of toluene under reflux, and allowed to cool down to 45° C. Then, 100 ml of ethyl acetate was added dropwise to perform crystallization, thereby obtaining crystals. N,N'-bis[{bis(4-tert-butylphenyl)amino}biphenyl-4'-yl]-N,N'-diphenyl-4,4''-diamino-p-terphenyl was obtained in an amount of 8.22 g. The yield was 61.1%, and the HPLC purity was 94.8%.

The crystals were purified by column chromatography (carrier: silica gel, eluate: toluene/n-hexane=1/2) to obtain 4.98 g (HPLC purity: 100.0%, column purification yield: 60.6%) of N,N'-bis[{bis(4-tert-butylphenyl)amino}biphenyl-4'-yl]-N,N'-diphenyl-4,4"-diamino-p-terphenyl. The melting point was 215.0° C. Identification of the product was performed by NMR analysis, elemental analysis and IR analysis. The elemental analysis values are as follows: carbon; measured value; 88.56% (theoretical value; 88.50%), hydrogen; measured value; 7.18% (theoretical value; 7.11%), nitrogen; measured value; 4.31% (theoretical value; 4.39%). The results of NMR analysis were as follows: 7.623 ppm (4H), 7.538-7.407 (12H), 7.275-7.035 ppm (38H), 1.313 ppm (36H).

Then, the physical properties of the respective compounds synthesized in the synthesis examples are collectively shown in Table 2.

TABLE 2

| | HPLC Purity | Tg | Decomposition Point | Melting Point |
|---|---|---|---|---|
| HTM-1 | 100.0% | 151.0° C. | 561.2° C. | 164.8° C. |
| HTM-2 | 100.0% | 154.5° C. | 572.3° C. | 189.3° C. |
| HTM-3 | 99.9% | 158.1° C. | 530.7° C. | 209.5° C. |
| HTM-4 | 99.8% | 156.5° C. | 568.1° C. | 173.1° C. |
| HTM-5 | 100.0% | 173.3° C. | 504.5° C. | 204.5° C. |
| HTM-6 | 100.0% | 181.0° C. | 524.1° C. | 215.0° C. |

<Preparation of EL Elements and Characteristic Evaluation>

In the following examples, the respective compounds synthesized in the above-mentioned examples were actually evaluated as EL elements, and the luminous characteristic, the stability of the luminous characteristic and the storage stability of the elements were studied. As shown in Table 1, the EL element was prepared by vapor depositing a hole injection layer 3, hole transport layer 4, a layer 5 used both as an electron transport layer and as a light emitting layer, a cathode buffer layer 6 and a cathode (aluminum electrode) 8 in this order on an ITO electrode previously formed as a transparent anode 2 on a glass substrate 1. A surface of the glass substrate on which the ITO electrode had been formed as a film was washed by UV & ozone treatment. This was set in a vapor depositing apparatus. Subsequently, copper phthalocyanine, the hole transport material of the invention, a purified alumiquinoline trimer, lithium fluoride and aluminum, respectively, were set in the vapor depositing apparatus, as the hole injection material, the hole transport material, the electron transportable light emitting material, the buffer layer and the cathode. Monitoring the film thickness with a crystal oscillator, the vapor deposition was performed at a vapor deposition speed of 2.00 angstroms/sec. The hole injection layer was 25 nm, the hole transport layer was 35 nm, the electron transportable light emitting layer was 1 nm, and the cathode was vapor deposited at a vapor deposition speed of 4.00 angstroms/sec up to 150 nm. These vapor depositions were all continuously performed without braking vacuum. Immediately after the preparation of the element, the electrode was taken out in dry nitrogen, and subsequently, characteristic measurement was carried out.

The luminous characteristic of the resulting element was defined by the luminous luminance at the time when a current of 100 mA/cm² was applied. Further, the luminous stability at the time of high temperature driving was compared using the element to which sealing treatment was not applied so that the difference due to the film characteristics of the hole transport material could be directly compared. Under a high temperature environment of 100° C., an initial voltage at which the element showed a luminous luminance of 1000 cd/m² was applied to measure a decrease in luminous luminance and changes in current value.

Example 7

Using HTM-1 (R1, R2, R3=H, n=3, melting point=164.8° C., Tg=151.0° C.) as the hole transport material, an ITO electrode washed by UV & ozone treatment, purified copper phthalocyanine as the hole injection material, a purified alumiquinoline trimer as the electron transportable light emitting material, lithium fluoride as the buffer layer, and aluminum as the cathode were set in a vapor depositing apparatus. Monitoring the film thickness with a crystal oscillator, the vapor deposition was performed at a vapor deposition speed of 2.00 angstroms/sec. The hole injection layer was 25 nm, the hole transport layer was 35 nm, the electron transportable light emitting layer was 1 nm, and the cathode was vapor deposited at a vapor deposition speed of 4.00 angstroms/sec up to 150 nm. These vapor depositions were all continuously performed without braking vacuum. Immediately after the preparation of the element, the electrode was taken out in dry nitrogen, adhered to a peltiert element, and heated to 100° C. Characteristic evaluation was conducted while keeping 100° C. The voltage at which an initial luminance of 1000 cd/m² was shown was 6.0 V. This element showed a maximum luminance of 1099 cd/m² at 11.6 mA after stabilization. Thereafter, the luminance decreased to 462 cd/m2 after 5 hours, to 321 cd/m2 after 8 hours, and to 214 cd/m2 after 12 hours. The driving current after 12 hours was 2.2 mA.

Comparative Example 1

For comparison, using a compound represented by N,N'-bis(naphthalene-1-yl)-N,N'-diphenylbenzidine (hereinafter a-NPD) which is the mainstream of the hole transport material at present, an EL element was prepared under the same conditions as in Example 7, and the characteristic thereof was examined by a similar method. This element showed an initial luminous of 1000 cd/m² at 5.0 V. This element showed a maximum luminance of 1089 cd/m² at 10.6 mA after stabilization. Although this element was lower in driving voltage than the element of Example 7, the luminous luminance showed 426 cd/m² after 5 hours, 282 cd/m² after 8 hours, and 184 cd/m² after 12 hours, and larger decreases in luminance were observed. Further, the driving current after 12 hours was 2.8 mA, which showed lower current efficiency than that of the element of Example 7.

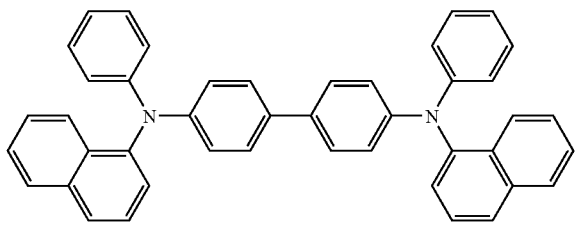

Example 8

In a manner similar to Example 7, there were prepared EL elements using HTM-2 (R1=phenyl group, R2, R3=H, n=3, melting point=189.3° C., Tg=154.5° C.), HTM-3

(R1=tert-butyl group, R2, R3=H, n=3, melting point=200.5° C., Tg=158.1° C.), HTM-4 (R1, R2, R3=H, n=4, melting point=173.1° C., Tg=156.5° C.), HTM-5 (R1, R2=phenyl group, R3=H, n=3, melting point=204.5° C., Tg=173.3° C.) and HTM-6 (R1, R2=4-tert-butylphenyl group, R3=H, n=3, melting point=215.0° C., Tg=181.0° C.), respectively, as the hole transport materials, and the characteristic thereof was evaluated. The results thereof are shown in Table 3. All the substitution positions of R1 and R2 in tetramine compounds HTM-1 to HTM-6 each connected through the above-mentioned plurality of phenyl groups are the p-position.

TABLE 3

| | Luminous Characteristic/cd · m$^{-2}$ |
|---|---|
| HTM-1 | 5300 |
| HTM-2 | 5500 |
| HTM-3 | 5500 |
| HTM-4 | 5300 |
| HTM-5 | 5400 |
| HTM-6 | 5450 |

Example 9

In the element prepared in Example 8, changes in a external appearance of the element at the time when it was stored under a high temperature of 100° C. were observed. The results thereof are shown in Table 4.

For α-NPD, the element became clouded by storage for 24 hours. In contrast, all the compounds synthesized in the invention kept transparency to show excellent amorphous film stability under high temperature environment.

TABLE 4

| | After 24 Hours | After 100 Hours |
|---|---|---|
| α-NPD | x | x |
| HTM-1 | o | o |
| HTM-2 | o | o |
| HTM-3 | o | o |
| HTM-4 | o | o |
| HTM-5 | o | o |
| HTM-6 | o | o | x: Clouded,
o: Not clouded

From the above, it is revealed that the elements synthesized in the invention, which are prepared using as the hole transport materials the tetramine compounds each connected through the plurality of phenyl groups, are excellent in heat stability.

Although the invention has been described in detail with reference to specific embodiments, it will be apparent to those skilled in the art that various changes and modifications may be made without departing from the spirit and scope of the invention.

The present application is based on Japanese Patent Application No. 2003-434432 filed on Dec. 26, 2003, the contents of which are incorporated herein by reference.

Industrial Applicability

The material of the invention is suitable as a material for an organic EL element requiring luminous stability at the time of high temperature driving which has been the largest problem of the conventional organic EL element.

The invention claimed is:

1. A tetramine compound represented by formula (1):

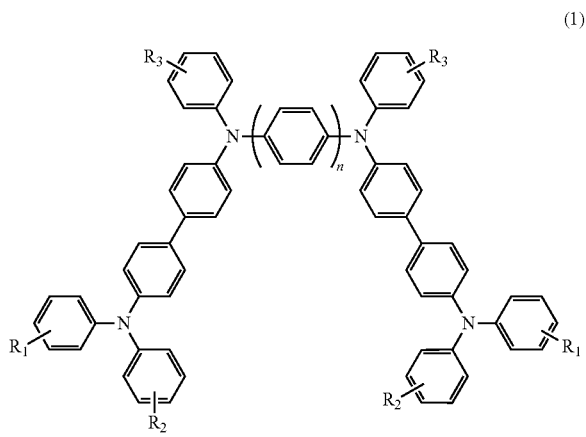

(1)

wherein R1, R2 and R3, which may be the same or different, each represents a hydrogen atom, a tertiary alkyl group having 4 to 8 carbon atoms, an unsubstituted aryl group or an aryl group substituted with a tertiary alkyl group having 4 to 8 carbon atoms, and n represents 3 or 4.

2. The tetramine compound according to claim 1, wherein the tetramine compound is at least one selected from the group consisting of:

N,N'-bis(4-diphenylaminobiphenyl-4'-yl)-N,N'-diphenyl-4,4"-diamino-p-terphenyl;

N,N'-bis[4-(4-biphenylylphenylamino)biphenyl-4'-yl]-N,N'-diphenyl-4,4"-diamino-p-terphenyl;

N,N'-bis[4-(4-tert-butyldiphenylamino)biphenyl-4'-yl]-N,N'-diphenyl-4,4"-diamino-p-terphenyl;

N,N'-bis(4-diphenylaminobiphenyl-4-yl)-N,N'-diphenyl-4,4'''-diamino-p-quaterphenyl;

N,N'-bis[4-{bis(biphenyl-4-yl)amino}biphenyl-4'-yl]-N,N'-diphenyl-4,4"-diamino-p-terphenyl; and N,N'-bis[{bis(4-tert-butylphenyl)amino}biphenyl-4'-yl]-N,N'-diphenyl-4,4"-diamino-p-terphenyl.

* * * * *